United States Patent
Liphardt (10) Patent No.: US 7,777,878 B2
(45) Date of Patent: Aug. 17, 2010

(54) APPLICATION OF DIGITAL LIGHT PROCESSOR IN SCANNING SPECTROMETER AND IMAGING ELLIPSOMETER AND THE LIKE SYSTEMS

(75) Inventor: Martin M. Liphardt, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 449 days.

(21) Appl. No.: 12/002,650

(22) Filed: Dec. 18, 2007

(65) Prior Publication Data

US 2009/0073449 A1 Mar. 19, 2009

Related U.S. Application Data

(60) Provisional application No. 60/875,599, filed on Dec. 19, 2006.

(51) Int. Cl.
 *G01J 3/08* (2006.01)
 *G01J 3/42* (2006.01)
 *G01J 4/04* (2006.01)
 *G01N 21/21* (2006.01)

(52) U.S. Cl. .................. 356/330; 356/328; 356/369

(58) Field of Classification Search .................. 356/310, 356/330
 See application file for complete search history.

(56) References Cited

U.S. PATENT DOCUMENTS

| | | | | |
|---|---|---|---|---|
| 4,114,366 A | | 9/1978 | Renner et al. ............... 368/68 |
| 5,504,575 A | * | 4/1996 | Stafford ...................... 356/330 |
| 5,909,559 A | | 6/1999 | So ............................... 710/307 |
| 5,932,119 A | | 8/1999 | Kaplan et al. .......... 219/121.68 |
| 6,061,049 A | | 5/2000 | Pettitt et al. .................. 345/691 |
| 6,105,119 A | | 8/2000 | Kerr et al. .................... 711/219 |
| 6,163,363 A | | 12/2000 | Nelson et al. ................. 355/32 |
| 6,179,489 B1 | | 1/2001 | So et al. ...................... 718/102 |
| 6,200,646 B1 | | 3/2001 | Neckers et al. ............... 427/510 |
| 6,259,153 B1 | | 7/2001 | Corisis ......................... 257/666 |
| 6,275,271 B1 | | 8/2001 | Hitomi et al. ................ 348/743 |
| 6,298,370 B1 | | 10/2001 | Tang et al. ................... 718/102 |
| 6,398,389 B1 | | 6/2002 | Bohler et al. ................ 362/293 |
| 6,459,425 B1 | | 10/2002 | Holub et al. ................. 345/207 |
| 6,496,477 B1 | | 12/2002 | Perkins et al. ............... 370/228 |
| 6,558,006 B2 | | 5/2003 | Ioka ............................ 353/94 |
| 6,583,921 B2 | | 6/2003 | Nelson ........................ 359/291 |
| 6,618,186 B2 | | 9/2003 | Kaeriyama ................... 359/292 |
| 6,619,804 B2 | | 9/2003 | Davis et al. .................... 353/98 |
| 6,654,516 B2 | | 11/2003 | So ............................... 385/27 |
| 6,658,063 B1 | | 12/2003 | Mizoguchi et al. .......... 375/260 |
| 6,663,560 B2 | * | 12/2003 | MacAulay et al. .......... 600/160 |
| 6,665,110 B2 | | 12/2003 | Pettitt ......................... 359/291 |
| 6,741,503 B1 | | 5/2004 | Farris et al. ............. 365/189.05 |
| 6,758,571 B2 | | 7/2004 | Heaton ........................ 359/872 |

(Continued)

FOREIGN PATENT DOCUMENTS

DE 10 2005 025 675 A1 * 11/2006

(Continued)

*Primary Examiner*—F. L Evans
(74) *Attorney, Agent, or Firm*—James D. Welch (57) ABSTRACT

Application of digital light processor (DLP) systems in monochromator, spectrophotometer or the like systems to mediate selection of individual wavelengths, and/or to image elected regions of a sample in an imaging ellipsometer, imaging polarimeter, imaging reflectometer, imaging spectrophotometer, and/or to provide chopped beams.

2 Claims, 6 Drawing Sheets

U.S. PATENT DOCUMENTS

| | | | |
|---|---|---|---|
| 6,781,094 B2 | 8/2004 | Harper | 219/121.72 |
| 6,842,549 B2 | 1/2005 | So | 385/15 |
| 6,856,446 B2 | 2/2005 | Di Carlo | 359/291 |
| 6,857,751 B2 | 2/2005 | Penn et al. | 353/97 |
| 6,870,660 B2 | 3/2005 | DiCarlo | 359/291 |
| 6,906,687 B2 | 6/2005 | Werner | 345/8 |
| 7,006,995 B1 | 2/2006 | Edenson et al. | 705/51 |
| 7,011,415 B2 | 3/2006 | DiCarlo et al. | 353/99 |
| 7,019,881 B2 | 3/2006 | Doherty et al. | 359/249 |
| 7,061,512 B2 | 6/2006 | Morgan et al. | 345/691 |
| 7,072,094 B2 | 7/2006 | Mezenner | 359/290 |
| 7,075,643 B2 | 7/2006 | Holub | 356/326 |
| 7,088,486 B2 | 8/2006 | DiCarlo | 359/224 |
| 7,116,459 B2 | 10/2006 | Huffman | 359/239 |
| 7,126,682 B2 | 10/2006 | Rowe et al. | 356/310 |
| 7,149,027 B2 | 12/2006 | Mehrl | 359/290 |
| 7,158,180 B2 | 1/2007 | Neidrich | 348/340 |
| 7,164,397 B2 | 1/2007 | Pettitt | 345/63 |
| 7,187,484 B2 | 3/2007 | Mehrl | 359/290 |
| 7,194,169 B2 | 3/2007 | Ikeda et al. | 385/115 |
| 7,196,740 B2 | 3/2007 | Huibers | 348/744 |
| 7,233,427 B2 | 6/2007 | Doherty et al. | 359/245 |
| 7,236,150 B2 | 6/2007 | Hui | 345/87 |
| 7,252,395 B2 | 8/2007 | DiCarlo et al. | 353/99 |
| 7,262,817 B2 | 8/2007 | Huibers | 348/771 |
| 7,265,766 B2 | 9/2007 | Kempf | 345/690 |
| 2001/0010843 A1 | 8/2001 | Garner | |
| 2002/0024640 A1 | 2/2002 | Ioka | |
| 2002/0041420 A1 | 4/2002 | Garner | |
| 2002/0057431 A1 | 5/2002 | Fateley et al. | |
| 2002/0081582 A1 | 6/2002 | Gao | |
| 2002/0171834 A1 | 11/2002 | Rowe et al. | |
| 2003/0003032 A1 | 1/2003 | Garner | |
| 2003/0019852 A1 | 1/2003 | Kaplan | |
| 2003/0020703 A1 | 1/2003 | Holub | |
| 2003/0054388 A1 | 3/2003 | Garner et al. | |
| 2003/0062802 A1 | 4/2003 | Battaglin et al. | |
| 2003/0138363 A1 | 7/2003 | Gao | |
| 2003/0143131 A1 | 7/2003 | Gao | |
| 2003/0186427 A1 | 10/2003 | Gao | |
| 2004/0008115 A1 | 1/2004 | Shih et al. | |
| 2004/0023368 A1 | 2/2004 | Gao | |
| 2004/0035690 A1 | 2/2004 | Gulari | |
| 2004/0155195 A1 * | 8/2004 | Maurel | 250/351 |
| 2004/0159641 A1 | 8/2004 | Kaplan | |
| 2005/0001820 A1 | 1/2005 | Lee | |
| 2005/0030328 A1 | 2/2005 | Yamada et al. | |
| 2005/0079386 A1 | 4/2005 | Brown | |
| 2005/0213092 A1 | 9/2005 | MacKinnon | |
| 2005/0251230 A1 | 11/2005 | MacKinnon et al. | |
| 2006/0019757 A1 | 1/2006 | Brunetti | |
| 2006/0028718 A1 | 2/2006 | Seel et al. | |
| 2006/0038188 A1 | 2/2006 | Erchak et al. | |
| 2006/0134669 A1 | 6/2006 | Casasanta et al. | |
| 2006/0197757 A1 | 9/2006 | Holub | |
| 2006/0220562 A1 | 10/2006 | Tsukamoto | |

FOREIGN PATENT DOCUMENTS

| | | |
|---|---|---|
| EP | 0916981 A1 * | 6/1999 |
| EP | 1258288 A2 * | 11/2002 |

* cited by examiner

APPLICATION OF DIGITAL LIGHT PROCESSOR IN SCANNING SPECTROMETER AND IMAGING ELLIPSOMETER AND THE LIKE SYSTEMS

CROSS-REFERENCE TO RELATED APPLICATIONS

This application Claims Benefit of Provisional Application Ser. No. 60/875,599 Filed Dec. 19, 2006.

TECHNICAL FIELD

The present invention relates to scanning spectrometers and imaging ellipsometer or the like systems, and more particularly to application of digital light processors (DLP) in such systems to mediate selection of individual wavelengths and/or to image selected regions of a sample and/or to provide chopped beams.

BACKGROUND

Spectrometers and monochromators are known which accept a beam of spectroscopic electromagnetic radiation and disperse it into a spatially expanded spectrum of wavelengths which are individually monitored. It is also known to direct a beam of electromagnetic radiation onto a surface area of a sample and then image electromagnetic radiation reflecting from different locations of the sample by an array of detectors, such as by use of an imaging ellipsometer or the like system. It is further known that chopping beams can provide benefits.

Further, Digital Light Processors (DLP) are known and have been applied to modulate homogeneous light applied thereto and generate images thereby, however, DLP's are not believed to have been applied to, for instance, process images projected thereonto, such as those produced by incident electromagnetic radiation reflecting from a sample in systems such as ellipsometers, polarimeters, reflectometers spectrophotometers or the like which typically apply detectors with a multiplicity of detector elements, such as charge coupled devices (CCD's).

U.S. patents which have been identified are:

U.S. Pat. Nos. 7,126,682; 7,265,766; 7,262,817; 7,252,395; 7,236,150; 7,233,427; 7,196,740; 7,194,169; 7,187,484; 7,164,397; 7,158,180; 7,149,027; 7,116,459; 7,088,486; 7,075,643; 7,072,094; 7,061,512; 7,019,881; 7,011,415; 7,006,995; 6,975,629; 6,965,470; 6,691,194; 6,937,382; 6,930,983; 6,906,852; 6,906,687; 6,870,660; 6,857,751; 6,856,446; 6,842,549; 6,781,094; 6,758,571; 6,741,503; 6,665,110; 6,654,516; 6,619,804; 6,618,186; 6,583,921; 6,558,006; 6,496,477; 6,459,425; 6,398,389; 6,298,370; 6,275,271; 6,259,153; 6,200,646; 6,179,489; 6,163,363; 6,105,119; 6,061,049; 5,932,119; 5,909,559; 5,658,559; 5,658,063; 4,114,366.

Published US applications which have been identified are:

US2005/001820; US2006/0220562; US2005/0079386; US2002/0024640; US2003/0143131; US2004/0023368; US2002/0081582; US2003/0138363; US2006/019757; US2004/0035690; US2003/0020703; US2006/0197757; US2004/0159641; US2003/0186427; US2003/0019852; US2002/0041420; US2003/0003032; US2001/0010843; US2005/0251230; US2005/0213092; US2006/0134669; US2002/0171834; US2003/0054388; US2006/0028718; US2003/062802; US2003/062802; US1999/041007; US2006/096310; US2005/030470; US2004/008115; US1999/010866; US1997/025177; US1999/063385; US2001/014460; US2005/030328; US2005/031292; US2002/084238.

Published Foreign Applications which have been identified are:

EP1070823; EP1258288; EP00916981; GB0232903.

What is to be new, novel and non-obvious is:
 to apply digital light processors (DLP) to the end that a spectrum of wavelengths, or a multiplicity of regions on a sample imaged onto a DLP, can be sequentially monitored by at least one detector element, sequential output from which is then interpreted or as corresponding to a sequence of different wavelengths and/or different locations on a sample surface; and
 to apply digital light processors (DLP) in systems such spectrometer, monochromator, and imaging ellipsometer, imaging polarimeter, imaging reflectometer, imaging spectrophotometer and the like imaging systems;
 to apply digital light processors (DLP) to chop electromagnetic beams.

DISCLOSURE OF THE INVENTION

The present invention comprises a scanning spectrometer or monochromator system, sequentially comprising:
 an input aperture;
 a dispersing means for spatially separating different wavelengths in electromagnetic radiation;
 a digital light processor;
 an imaging means; and
 a selection from the group consisting of:
  at least one detector element;
  at least one optical fiber; and
  an exit aperture.

Said digital light processor comprises an array of a multiplicity of microscopic mirrors, each said microscopic mirror being controllable to reflect incident electromagnetic radiation along at least two different loci. In use said input aperture is positioned to receive spectroscopic electromagnetic radiation and provide at least a portion thereof to said dispersing means, which dispersing means serves to disperse said wavelengths into a spatially expanded spectrum of wavelengths and direct them to said digital light processor such that different wavelengths impinge on different microscopic mirrors therein. At least one of said microscopic mirrors can be oriented to reflectively direct electromagnetic radiation of a wavelength incident thereupon into said at least one detector element or optical fiber, while other microscopic mirrors in said digital light processor are oriented to reflectively direct electromagnetic radiation, (eg. of other wavelengths), away from said at least one detector element or optical fiber. It is noted that where a detector element is present the system is applicable as a scanning spectrometer, and where an optical fiber is present the system is a monochromator system which can provide selected wavelengths to a distal end thereof.

It is noted that the scanning spectrometer or monochromator system can comprise an imaging means which is selected from the group consisting of:
 it is telecentric having an entrance and/or exit pupil at infinity; and
 it is non-telecentric;

which can be a mirror, a lens, a system of lenses or a system of mirrors or combinations of at least one mirror and at least one lens, said selection typically being fashioned to reduce aberrations. Further, the dispersion means can be a concave grating such as a produced by a holographic process, or a flat grating or a prism or functional equivalent. When present, the exit aperture will typically direct electromagnetic radiation exiting therefrom to a means for detecting it. As regards the telecentric imaging means, it is noted that placing a source of electromagnetic radiation at its focal point causes collimated electromagnetic radiation to exit therefrom, and causing collimated electromagnetic radiation to enter thereinto results in its being focused at the focal point thereof.

It is also noted that said scanning spectrometer or monochromator system can provide that the rates at which different microscopic mirrors (MM) thereof operate are selected from the group consisting of:

the duty cycles of all microscopic mirrors (MM) are the same;
    the duty cycles of different microscopic mirrors (MM) are different; and
    the duty cycles of different microscopic mirrors (MM) are selected so as to provide a more homogeneous intensity output;

where "duty cycle" refers to the relationship between "on" and "off" times during which electromagnetic radiation is directed toward and away from the at least one detector element; at least one optical fiber; or said exit aperture.

A method of scanning a multiplicity of wavelengths and providing them as a sequential output from at least one detector element, optical fiber or exit aperture, comprises the steps of:

a) providing a system sequentially comprising:
    an input aperture;
    a dispersing means for spatially separating different wavelengths in electromagnetic radiation;
    a digital light processor;
    a imaging means for directing electromagnetic radiation; and
    a selection from the group of:
      at least one detector element;
      at least one optical fiber; and
      an exit aperture;
  said digital light processor comprising an array of a multiplicity of microscopic mirrors, each said microscopic mirror being controllable to reflect incident electromagnetic radiation along at least two different loci;
  such that in use said input aperture is positioned to receive spectroscopic electromagnetic radiation and provide at least a portion thereof to said dispersing means, which dispersing means serves to disperse said wavelengths into a spatially expanded spectrum of wavelengths and direct them to said digital light processor such that different wavelengths impinge on different microscopic mirrors, at least one of which microscopic mirrors is oriented to reflectively direct electromagnetic radiation of a wavelength incident thereupon into said at least one detector element, optical fiber or exit aperture, while other microscopic mirrors in said digital light processor are oriented to reflectively direct electromagnetic radiation, (eg. of other wavelengths), away from said at least one detector element, optical fiber or exit aperture;
  b) causing spectroscopic electromagnetic radiation to pass through said input aperture, impinge on said dispersing means, and reflect from said dispersing means as a dispersed spatially expanded spectrum of wavelengths, such that different wavelengths impinge on different microscopic mirrors in said digital light processor;
  c) causing at least one microscopic mirror in said digital light processor to be oriented to reflectively direct electromagnetic radiation of a first wavelength, which impinges thereupon, into said at least one detector element, optical fiber or exit aperture while reflectively directing electromagnetic radiation incident on other microscopic mirrors away from said at least one detector element, optical fiber or exit aperture;
  d) causing the microscopic mirror oriented to reflectively direct electromagnetic which impinges thereupon into said at least one detector element, optical fiber or exit aperture in step c, to become reoriented so that electromagnetic which impinges thereupon is redirected so that it does not enter said at least one detector element, optical fiber or exit aperture, along with causing at least one other microscopic mirror in said digital light processor to be oriented to reflectively direct electromagnetic radiation of another wavelength, which impinges thereupon, into said at least one detector element or optical fiber while reflectively directing electromagnetic radiation incident on other microscopic mirrors away from said at least one detector element, optical fiber or exit aperture; and monitoring the sequential output of said at least one detector element, optical fiber or exit aperture as the orientations of said microscopic mirrors are changed and interpreting said output as a sequence of different wavelengths.

In the foregoing it is important to realize that while use thereof is not prohibited, no multiple element detector such as a charge coupled device (CCD) is necessary. A single detector element can be applied to sequentially monitor electromagnetic radiation directed thereinto by a Digital Light Processor.

The present invention also comprises an imaging system, such as an imaging ellipsometer, an imaging polarimeter, an imaging reflectometer, and imaging spectrophotometer or the like system, sequentially comprising:

a source of electromagnetic radiation;
  a collecting means for directing electromagnetic radiation, (eg. a collimating lens);
  a stage for supporting a sample;
  a first focusing means, (eg. a lens);
  a digital light processor;
  a second focusing means, (eg. a lens);
  a detector element; and
  said imaging system further optionally comprising polarization state generation and polarization state analysis means between said source of electromagnetic radiation and said sample, and between said sample and said at least one detector element, respectively;

Said digital light processor comprising an array of a multiplicity of microscopic mirrors, each said microscopic mirror being controllable to reflect incident electromagnetic radiation along at least two different loci. In use said source of electromagnetic radiation provides an expanding beam of electromagnetic radiation to said collecting means, which in turn directs electromagnetic radiation onto a sample placed on said stage for supporting a sample; and such that said first focusing means focuses collected electromagnetic radiation reflecting from said sample. At least one of said microscopic mirrors in said digital light processor is caused to be oriented to direct electromagnetic radiation incident thereupon to said second focusing means, which in turn focuses electromagnetic radiation provided thereto from said at least one microscopic mirror, onto said at detector element.

It is noted that the detector element can be one element of a multiple element detector, or can comprise a light fiber or exit aperture.

A modified imaging system, (wherein said digital light processor is a first digital light processor); which further comprises, between said first digital light processor and said at least one detector element, a spectrometer sequentially comprising:
   a dispersing means, (eg. a grating), for spatially separating different wavelengths in electromagnetic radiation; and
   a second digital light processor;

such that said dispersing means receives electromagnetic radiation from said first digital light processor and directs it to said dispersing means which provides electromagnetic radiation to said second digital light processor and directs it to said at least one detector element.

A present invention method of imaging a sample and providing said image as a sequential output from a detector element, comprises the steps of:
   a) providing an imaging system as just described;
   b) causing said source of electromagnetic radiation to provide an expanding beam of electromagnetic radiation to said collecting means, which in turn directs electromagnetic radiation onto a sample placed on said stage for supporting a sample; and causing said first focusing means to focus collected electromagnetic radiation reflecting from said sample;
   c) causing at least one of said microscopic mirrors in said digital light processor to be oriented to direct electromagnetic radiation incident thereupon to said second focusing means, which in turn focuses electromagnetic radiation provided thereto from said at least one microscopic mirror onto said detector element.

Said method can further comprise:
   d) causing said at least one microscopic mirror in said digital light processor which was caused to be oriented to direct electromagnetic radiation incident thereupon to said second focusing means in step c, to be reoriented so as to direct incident electromagnetic radiation away from said detector element; and causing at least one other microscopic mirror in said digital light processor to be oriented to direct electromagnetic radiation incident thereupon to said second focusing means which in turn focuses electromagnetic radiation provided thereto from said at least one microscopic mirror onto said detector element, which in turn focuses electromagnetic radiation provided thereto from said at least one microscopic mirror onto said detector element;

monitoring the sequential output of said detector element as the orientations of said microscopic mirrors are changed and interpreting said output as a sequence of images of different locations on said sample.

Said method can also comprise combining data obtained by practice of steps a-d to provide a composite image.

In the foregoing it is important to realize that no multiple element detector such as a charge coupled device (CCD) is necessary. A single detector element can sequentially monitor electromagnetic radiation directed thereinto by a operation of a digital light processor. It is also noted that if electromagnetic radiation reflected by a digital light processor mirror is spectroscopic, it is possible to spatially disperse the wavelengths, such as by applying the electromagnetic radiation to a diffraction dispersing means or functional equivalent, and sequentially or simultaneously direct different wavelengths to different single element detectors.

Another method, of providing a beam of relatively uniform intensity over a wide range of wavelengths, comprises the steps of:
   a) providing a system comprising:
      a source of spectroscopic electromagnetic radiation having a non-uniform intensity vs. wavelength characteristic;
      a dispersion means; and,
      a digital light processor;

said digital light processor comprising an array of a multiplicity of microscopic mirrors, each said microscopic mirror being controllable to reflect incident electromagnetic radiation along at least two different loci;
   b) causing said source of spectroscopic electromagnetic radiation having a non-uniform intensity vs. wavelength characteristic to impinge on said dispersion means and exit therefrom as a spectrum of spatially separated wavelengths which are directed to impinge on said digital light processor;
   c) causing microscopic mirrors in said digital light processor to be oriented such that more thereof receiving wavelengths having a relatively low intensity direct electromagnetic radiation incident thereon to a detector, while less thereof are oriented to direct wavelengths having a relatively high intensity are so directed.

A method of providing a chopped beam comprises the steps of:
   a) providing a source of a beam of electromagnetic radiation and a digital light processor comprising an array of a multiplicity of microscopic mirrors, each said microscopic mirror being controllable to reflect incident electromagnetic radiation along at least two different loci;
   b) causing said source to provide a beam directed to impinge on said digital light processor and monitoring a beam reflected therefrom which causing at least some of said microscopic mirrors to quickly change orientation.

Chopped beams are beneficial as, for instance, they can be detected with better stability, and can be used in lighted rooms using a demodulation technique.

It is also noted that not all microscopic mirrors have to be quickly changed at the same rapid changing rate. For instance, an apodizing filter can be approximated by causing microscopic mirrors that reflect the outer perimeter of a beam at a different rate than are microscopic mirrors in the more central regions. This can, for instance, cause more or less overall intensity to reflect from the periphery of the beam than from the more central regions via duty cycling.

It is to be understood that any of the foregoing Methods can also involve obtaining data by application of a data detector, and performing at least one selection from the group consisting of:
   storing at least some data provided by said data detector in machine readable media;
   analyzing at least some of the data provided by said data detector and storing at least some of the results of said analysis in machine readable media;
   displaying at least some data provided by said data detector by electronic and/or non-electronic means;
   analyzing at least some of the data provided by said data detector and displaying at least some of the results of said analysis by electronic and/or non-electronic means;
   causing at least some data provided by said data detector to produce a signal which is applied to provide a concrete and tangible result;
   analyzing at least some of the data provided by said data detector and causing at least some thereof to produce a signal which is applied to provide a concrete and tangible result.

Further, it is to be understood that those skilled in the relevant art agree that electromagnetic radiation is altered in a concrete and tangible way by interaction with, (eg. by reflecting from and/or transmitting through), a material system. This can be, for instance, at the quantum level and/or effects on intensity and/or beam polarization state, which are be changed thereby.

The invention will be better understood by reference to the Detailed Description Section, in combination with the Drawings.

DETAILED DESCRIPTION

Figure 1A:
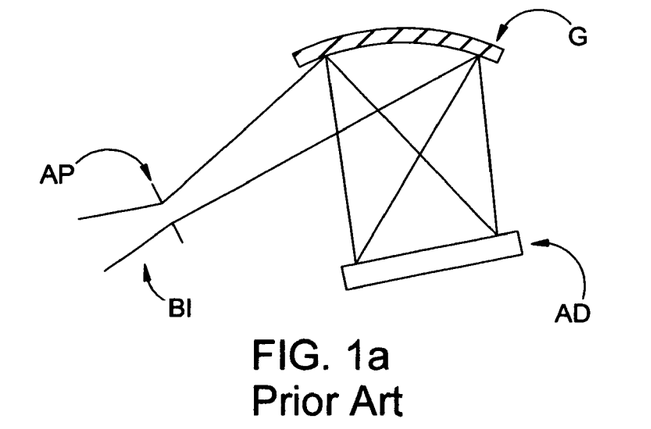
FIG. 1a shows a Prior Art Spectrometer.

Turning now to the Drawings, FIG. 1a shows a Prior Art Spectrometer comprised of an Input Aperture (AP), a Grating (G) and an Array Detector (AD) such as a CCD array.

Figure 1B:
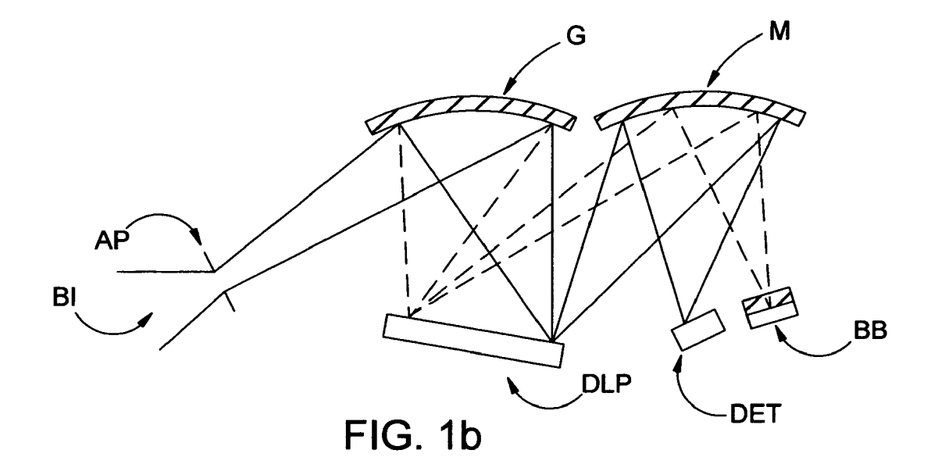
FIG. 1b shows a Present Invention Scanning Spectrometer System.

FIG. 1b shows a Present Invention Scanning Spectrometer System sequentially comprising:
 an Input Aperture (AP);
 a Dispersing Means (G) for spatially separating different wavelengths in electromagnetic radiation;
 a Digital Light Processor (DLP);
 an Imaging Means (M) for directing electromagnetic radiation; and
 at least one Detector Element (DET).

Note that the at least one Detector Element (DET) can be a selection from the group consisting of:
 said at least one Detector Element (DET);
 at least one Optical Fiber (OF); and
 an Exit Aperture (EA).

Note, if the at least one Detector (DET) Element is replaced by at least one Optical Fiber, FIG. 1b can be considered an Monochromator that provides selected wavelengths at a distal end thereof.

Figure 1C:
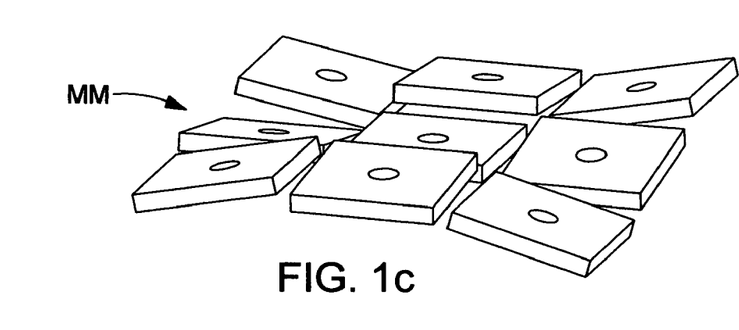
FIG. 1c shows nine elements of a Texas Instruments Digital Light Processor (DLP) system, in various states.

It is noted that said Digital Light Processor (DLP) comprises an array of a multiplicity of Microscopic Mirrors (MM), (see FIG. 1c), each said Microscopic Mirror being controllable to reflect incident electromagnetic radiation along at least two different loci. FIG. 1c shows nine elements of a Texas Instruments, (Trademark), Digital Light Processor (DLP) system in various states.

Returning to FIG. 1b it should be appreciated that in use said Input Aperture (AP) is positioned to receive Spectroscopic Electromagnetic Radiation (BI) and provide at least a portion thereof to said Dispersing Means (G), (eg. a Concave Grating), which Dispersing Means (G) serves to disperse said wavelengths into a spatially expanded spectrum of wavelengths and direct them to said Digital Light Processor (DLP) such that different wavelengths impinge on different Microscopic Mirrors (MM) therein. At least one of said Microscopic Mirrors (MM) is then oriented to reflectively direct electromagnetic radiation of a wavelength incident thereupon toward said Imaging Means (M) which directs it into said Detector Element (DET). Other Microscopic Mirrors (MM) in said Digital Light Processor (DLP) are oriented to reflectively direct electromagnetic radiation, (eg. of other wavelengths), away from said Detector Element (DET).

Figure 2A:
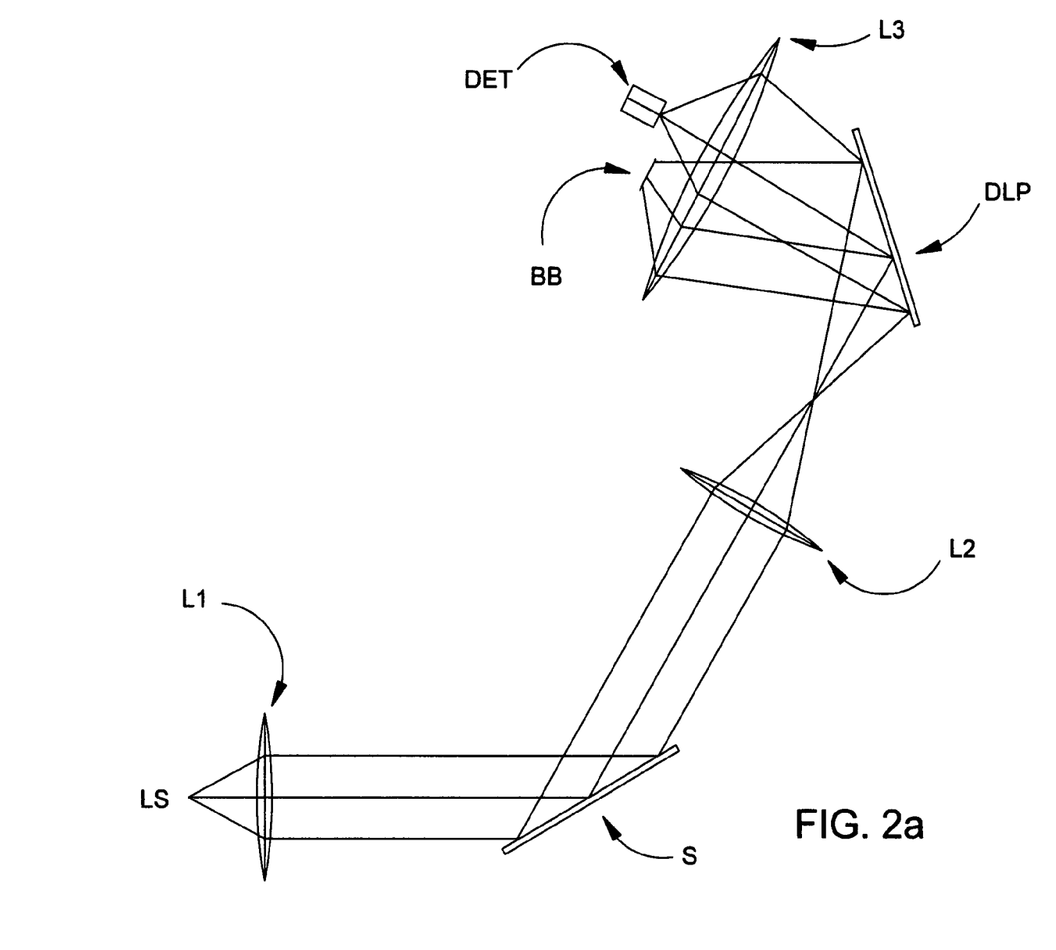
FIG. 2a shows a Present Invention Imaging. Ellipsometer or the like system with more than one microscopic mirror (MM) directing electromagnetic radiation directed to a detector element (DET).

FIG. 2a shows a Present Invention Imaging System such as an imaging ellipsometer, an imaging polarimeter, an imaging reflectometer, and imaging spectrophotometer or the like system, sequentially comprising:
 a Source (LS) of electromagnetic radiation;
 a Collecting Means (L1);
 a Stage (STG) for supporting a Sample (S);
 a First Focusing Means (L2);
 a Digital Light Processor (DLP);
 a Second Focusing Means (L3); and
 at least one Detector Element (DET).
 said imaging system further optionally comprising Polarization State Generation (PSG) and Polarization State Analysis (PSA) means between said source of electromagnetic radiation and said sample, and between said sample and said at least one detector element, respectively.

Figure 2B:
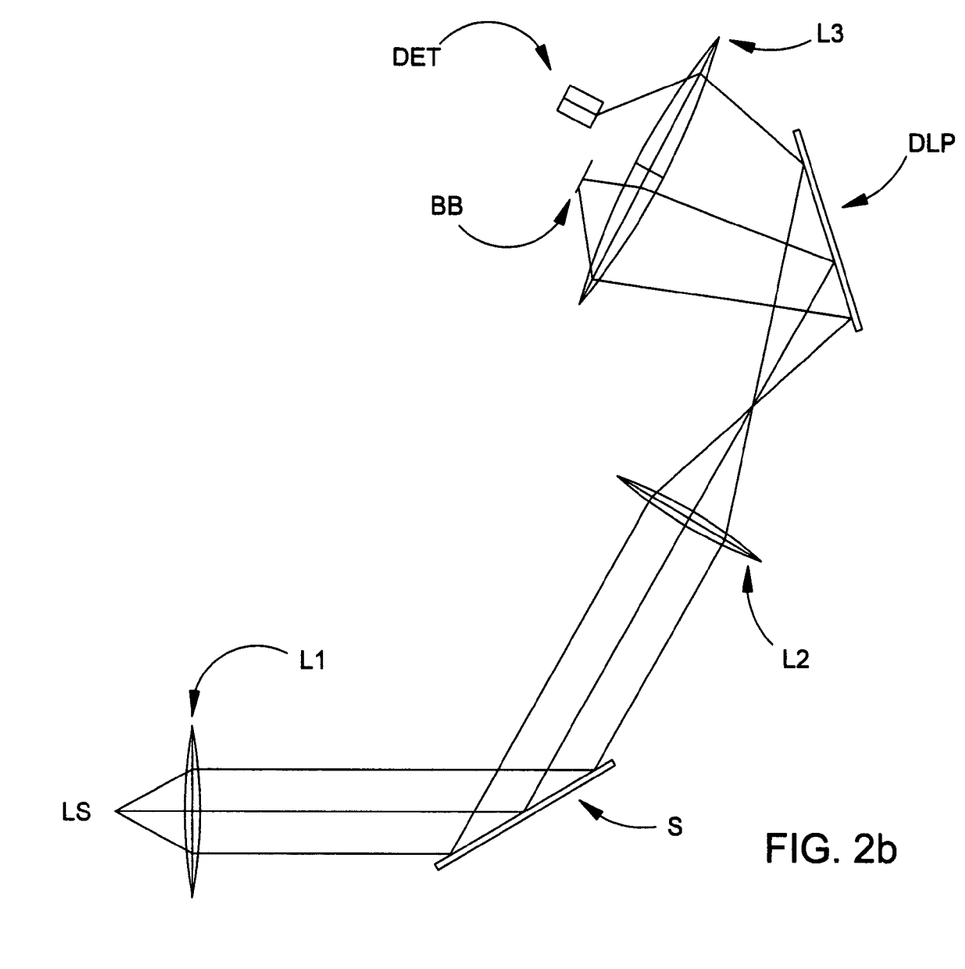
FIG. 2b shows FIG. 2a with one microscopic mirror (MM) directing electromagnetic radiation directed to a detector element (DET) and with other microscopic mirrors (MM) directing electromagnetic radiation to a beam block (BB).

Note that multiple (DLP) Microscopic Mirrors (MM) direct electromagnetic radiation to the detector (DET) in FIG. 2a. FIG. 2b is included to show FIG. 2a with only one Microscopic Mirror (MM) directing electromagnetic radiation directed to a detector element and with other microscopic mirrors directing electromagnetic radiation to a Beam Block (BB). This is important in imaging applications where data from a single location on a sample is desired.

Figure 4:
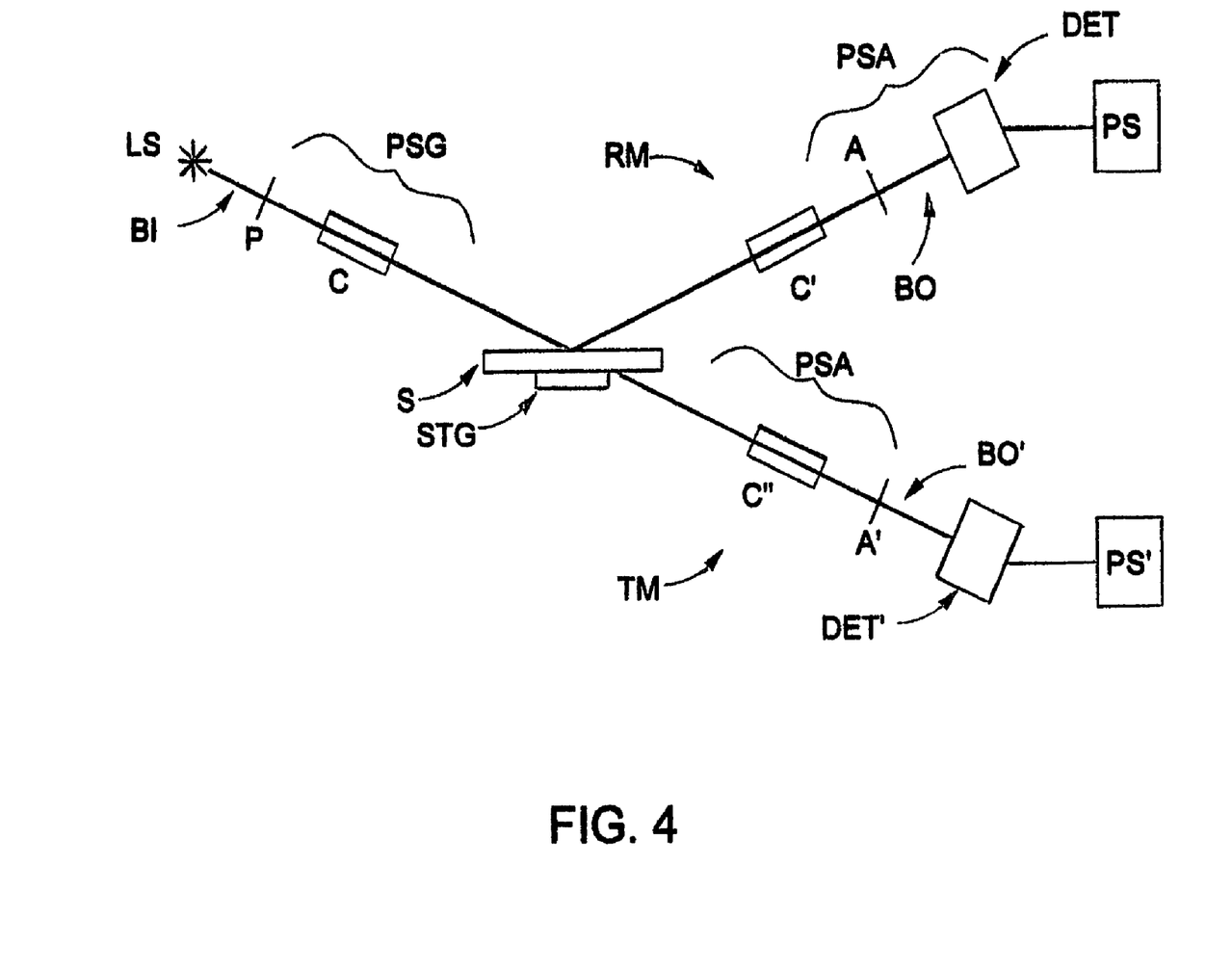
FIG. 4 demonstrates an ellipsometer system for general disclosure.

As demonstrated in FIG. 4, said (PSG) can comprise a Polarizing Element (P), optionally in combination with a Compensator (C), and the (PSA) can comprise an Analyzing Element (P), optionally in combination with a Compensator (C') (C'').

As described above, said Digital Light Processor (DLP) comprises an array of a multiplicity of Microscopic Mirrors (MM) as demonstrated in FIG. 1c. Again, each said Microscopic Mirror (MM) is controllable to reflect incident electromagnetic radiation along at least two different loci.

Returning to FIGS. 2a and 2b, in use said Source (LS) of electromagnetic radiation provides an expanding beam of electromagnetic radiation (BI) to said Collecting Means (L1), which in turn directs electromagnetic radiation onto a Sample (S) placed on said stage for supporting a sample. Said First Focusing Lens (L2) focuses collected electromagnetic radiation reflecting from said Sample (S) to a point (FP) between said First Focusing Lens (L2) and said Digital Light Processor (DLP) such that electromagnetic radiation impinges on said Digital Light Processor (DLP) as an expanding beam. At least one of said Microscopic Mirrors (MM) in said Digital Light Processor (DLP) is caused to be oriented to direct electromagnetic radiation incident thereupon to said Second Focusing Means (L3), which in turn focuses electromagnetic radiation provided thereto from said at least one Microscopic Mirror (MM) onto said at least one Detector Element (DET). Note that other of said Digital Light Processor (DLP) Microscopic Mirrors (MM) are simultaneously set to direct electromagnetic radiation away from said at least one Detector Element (DET), and optionally at an absorbing Beam Block Means (BB) which serves to absorb and prevent stray electromagnetic radiation from entering said at least one Detector Element (DET). Note that the focus point of (L2) can be between said First Focusing Means (L2) and the Digital Light Processor (DLP) so that the beam is expanding as it approaches the later.

Figure 2C:
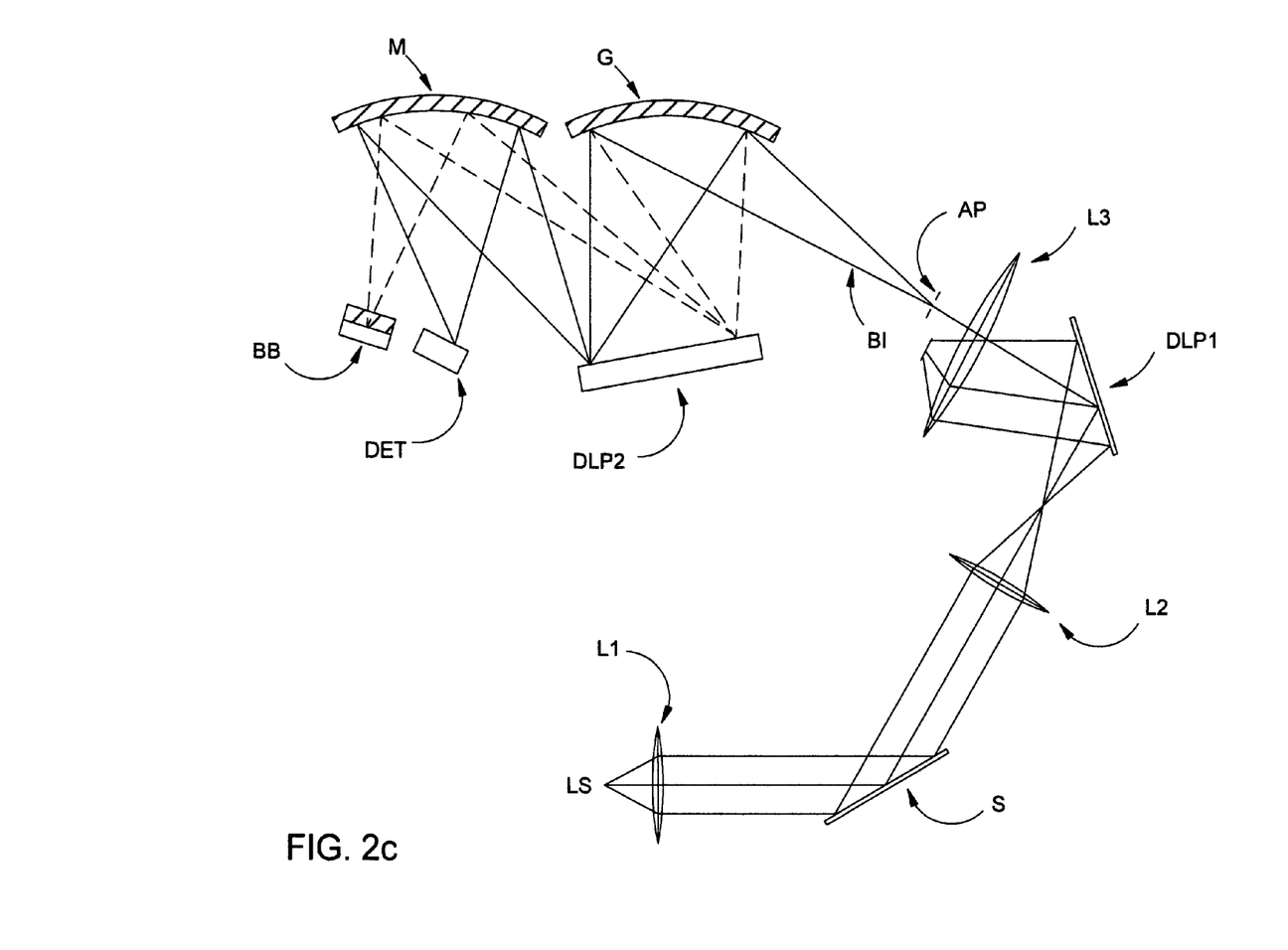
FIG. 2c shows a Present Invention Imaging Ellipsometer or the like system combined with a Scanning Spectrometer System.

FIG. 2c shows the system of FIGS. 2a and 2b, combined with the Wavelength Scanning system of FIG. 1b. This combination is useful in monitoring the wavelength spectrum of electromagnetic radiation reflected from specific Digital Light Processor (DLP) Microscopic Mirrors (MM), which monitor a specific location on a Sample (S). The same identifiers used in FIGS. 2a and 1b are applicable in FIG. 2c.

Figure 3A:
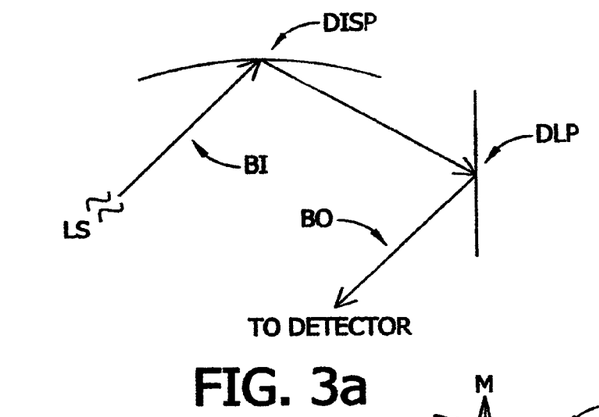
FIGS. 3a and 3b show a system for providing a beam of electromagnetic radiation having a relatively uniform intensity over a wide range of wavelengths.
Figure 3B:
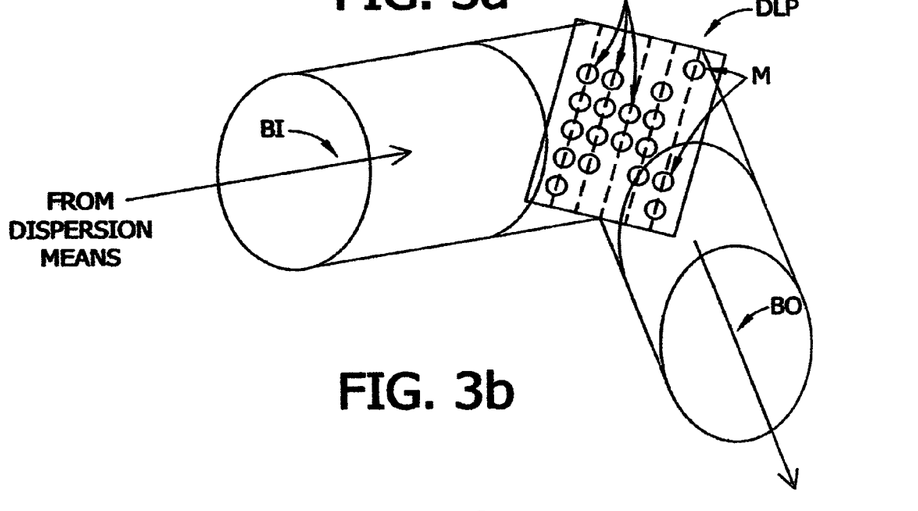
Figure 3C:
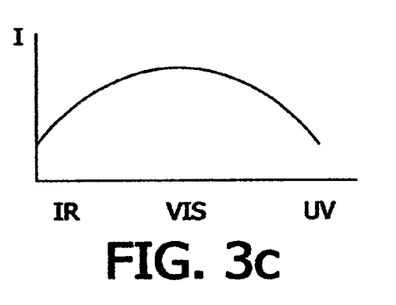
FIGS. 3c and 3d show plots of intensity vs. wavelength spectrum of the Source (LS) and a spectrum exiting the (DLP) possible using the system of FIGS. 3a and 3b.
Figure 3D:
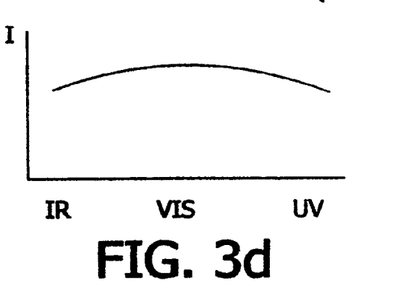

FIGS. 3a and 3b show a system for providing a beam of electromagnetic radiation having a relatively uniform intensity over a wide range of wavelengths. FIG. 3a shows a Spectroscopic Source (LS) of a beam of electromagnetic radiation (BI) which is directed to a Dispersion means (DISP). Electromagnetic radiation exiting said Dispersion means (DISP) is characterized by having a spatially separated wavelength spectrum. Said dispersed wavelengths are directed to a Digital Light Processor (DLP), in which Microscopic Mirrors (MM) thereof are operated so that so that those receiving wavelengths of relatively low intensity reflect wavelengths toward a Detector (DET) at a duty cycle with a relatively longer "on" than "off" duty cycle than do said Microscopic Mirrors (MM) which receive wavelengths of a higher intensity. FIG. 3b shows less Microscopic Mirrors (M) in a central region of the (DLP) are oriented to direct impinging electromagnetic radiation (BI) toward a Detector as (BO) than are Microscopic Mirrors (M) at the sides of the (DLP). This configuration would be beneficial where, for instance, the central portion of the (DLP) received Visible wavelengths and the laterally positioned Microscopic Mirrors (M) received (IR) and (UV) wavelengths and the Source (LS) provided higher intensity Visible (VIS) wavelengths and lower intensity Infrared (IR) and Ultraviolet (UV) wavelengths. FIGS. 3c and 3d show exemplary plots of Intensity vs. Wavelength to demonstrate the effect. FIG. 3c demonstrate the spectrum of the Source (LS) provided electromagnetic radiation (BI) and FIG. 3d a spectrum of electromagnetic radiation (BO) exiting the (DLP).

FIG. 4 is included to generally disclose a representative ellipsometer system. Note that a Source (LS) of electromagnetic radiation provides a beam (BI) of electromagnetic radiation which passes through a Polarizer (P) and Compensator (C) before interacting with a Sample either by reflection (RM) or transmission (TM). Said reflection mode (RM) beam is shown to pass through a Compensator (C') and an Analyzer (A) then enter a Detector (DET) as beam (BO), which can produce a signal and provide it to some system for producing a concrete and tangible result (PS). The transmission mode (TM) beam likewise is shown to pass through a Compensator (C") and an Analyzer (A') then enter a Detector (DET') as beam (BO'), which can produce a signal and provide it to some system for producing a concrete and tangible result (PS'). It is to be appreciated that the Polarizer (P) can independently, or in combination with the Compensator (C), comprise a Polarization State Generator (PSG). Likewise the Analyzer (A) (A') can independently, or in combination with the Compensator (C') (C"), comprise a Polarization State Analyzer (PSA). A present invention imaging ellipsometer has the Digital Light Processor (DLP) included as alluded to above.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. An imaging spectrometer system sequentially comprising:
   a source (LS) of electromagnetic radiation;
   a collecting means (L1) for directing electromagnetic radiation;
   a stage (STG) for supporting a sample (S);
   a first focusing means (L2);
   a first digital light processor (DLP); and
   a second focusing means (L3);
   said imaging system further optionally comprising polarization state generation and polarization state analysis means between said source of electromagnetic radiation and said sample, and after said sample, respectively;
   said first digital light processor (DLP) comprising an array of a multiplicity of microscopic mirrors (MM), each said microscopic mirror (MM) being controllable to reflect incident electromagnetic radiation along at least two different loci;
   said collecting means, first focusing means and second focusing means all being selected from the group consisting of:
      a lens;
      a mirror;
      a system of lenses;
      a system of mirrors;
      a system comprising at least one lens and at least one mirror;
   such that in use said source (LS) of electromagnetic radiation provides an expanding beam (BI) of electromagnetic radiation to said collecting means (L1), which in turn directs electromagnetic radiation onto a sample (S) placed on said stage (STG) for supporting a sample (S); and such that said first focusing means (L2) generates an image of said sample (S) on said first digital light processor (DLP);
   at least one of said microscopic mirrors (MM) in said first digital light processor (DLP) being caused to be oriented to direct electromagnetic radiation incident thereupon to said second focusing means (L3), which in turn focuses electromagnetic radiation provided thereto from said at least one microscopic mirror (MM) in a desired direction while other of said microscopic mirrors (MM) direct electromagnetic radiation away therefrom;
   said imaging system further comprising, after said first digital light processor (DLP), a spectrometer sequentially comprising:
      a dispersing means (G) for spatially separating different wavelengths in electromagnetic radiation;
      a second digital light processor (DLP2); and
      at least one detector element (DET);
   such that said dispersing means (G) receives electromagnetic radiation from said first digital light processor (DLP) which is directed in said desired direction, and directs it to said dispersing means (G) which provides electromagnetic radiation to said second digital light processor (DLP2), which directs selected wavelengths into said at least one detector element (DET) while directing other wavelengths away therefrom.

2. A method of investigating how specific wavelengths in a spectroscopic beam of electromagnetic radiation which interact with an imaged spot on a sample, are affected by said interaction therewith comprising:

- a) providing an imaging spectrometer system sequentially comprising:
  - a source (LS) of electromagnetic radiation;
  - a collecting means (L1) for directing electromagnetic radiation;
  - a stage (STG) for supporting a sample (S);
  - a first focusing means (L2);
  - a first digital light processor (DLP); and
  - a second focusing means (L3);
  - said imaging system further optionally comprising polarization state generation and polarization state analysis means between said source of electromagnetic radiation and said sample, and after said sample, respectively;
  - said first digital light processor (DLP) comprising an array of a multiplicity of microscopic mirrors (MM), each said microscopic mirror (MM) being controllable to reflect incident electromagnetic radiation along at least two different loci;
  - said collecting means, first focusing means and second focusing means all being selected from the group consisting of:
    - a lens;
    - a mirror;
    - a system of lenses;
    - a system of mirrors;
    - a system comprising at least one lens and at least one mirror;
  - such that in use said source (LS) of electromagnetic radiation provides an expanding beam (BI) of electromagnetic radiation to said collecting means (L1), which in turn directs electromagnetic radiation onto a sample (S) placed on said stage (STG) for supporting a sample (S); and such that said first focusing means (L2) generates an image of said sample (S) on said first digital light processor (DLP);
  - at least one of said microscopic mirrors (MM) in said first digital light processor (DLP) being caused to be oriented to direct electromagnetic radiation incident thereupon to said second focusing means (L3), which in turn focuses electromagnetic radiation provided thereto from said at least one microscopic mirror (MM) in a desired direction while other of said microscopic mirrors (MM) direct electromagnetic radiation away therefrom;
  - said imaging system further comprising, after said first digital light processor (DLP), a spectrometer sequentially comprising:
    - a dispersing means (G) for spatially separating different wavelengths in electromagnetic radiation;
    - a second digital light processor (DLP2); and
    - at least one detector element (DET);
  - such that said dispersing means (G) receives electromagnetic radiation from said first digital light processor (DLP) which is directed in said desired direction, and directs it to said dispersing means (G) which provides electromagnetic radiation to said second digital light processor (DLP2), which directs selected wavelengths into said at least one detector element (DET) while directing other wavelengths away therefrom;
- b) causing said source (LS) of electromagnetic radiation to provide a spectroscopic beam of electromagnetic radiation and direct it toward said collecting means (L1) for directing electromagnetic radiation such that it is directed onto a sample stage (STG) for supporting a sample (S), interact with said first focusing means (L2), said first digital light processor (DLP), and said second focusing means (L3) which in turn focuses electromagnetic radiation provided thereto from said at least one microscopic mirror (MM) in a desired direction while other of said microscopic mirrors (MM) direct electromagnetic radiation away therefrom, such that said electromagnetic radiation directed in said desired direction interacts with a dispersing means (G) for spatially separating different wavelengths in electromagnetic radiation, a second digital light processor (DLP2); and at least one detector element (DET);
- c) causing said first digital light processor (DLP) to direct electromagnetic radiation corresponding to an imaged location on said sample toward said collecting means (L1), and causing said second digital light processor (DLP2) to direct specific wavelengths into said lest one detector element;
- d) obtaining output from said at least one detector element and analyzing at least some of the data provided by said at least one detector element.

* * * * *